United States Patent [19]

Hartmann

[11] Plant 4,949

[45] Nov. 16, 1982

[54] CHRYSANTHEMUM PLANT

[76] Inventor: Fred B. Hartmann, 867 Dickson St., Kirkwood, Mo. 63122

[21] Appl. No.: 241,722

[22] Filed: Mar. 9, 1981

[51] Int. Cl.[3] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Koch

[57] ABSTRACT

A dark yellow standard chrysanthemum selection of the variety Deep Yellow Hartmann's Dignity, particularly distinguished by its dark yellow color, which is solid on the entire flower including the underside of the petals, and by its more compact flower head and increased petallage when compared with the parent cultivar.

2 Drawing Figures

The present invention comprises a new and distinct cultivar of *Chrysanthemum morifolium,* Ramat., hereinafter referred to by the cultivar name Hartmann's Gold Dignity.

The new cultivar was observed and selected in a cultivated field at Kirkwood, Mo. as a mutation of the standard chrysanthemum Deep Yellow Hartmann's Dignity, disclosed in my pending application Ser. No. 123,788, filed Feb. 22, 1980. The parent Deep Yellow Hartmann's Dignity in turn was a mutation of the cultivar Hartmann's Yellow Dignity, disclosed in U.S. Plant Pat. No. 4,477 granted Nov. 6, 1979 to Kerry S. Petvsky. The new cultivar was selected for its more compact flowerhead and increased petallage when compared with the parent cultivar Deep Yellow Hartmann's Dignity. Like its parent, the new cultivar is also importantly characterized by its solid, relatively deep yellow color on all the petals, including the underside of the petals. Asexual reproduction by vegetative cuttings taken by me at Kirkwood, Mo. has demonstrated that the characteristics of Hartmann's Gold Dignity are firmly fixed and are retained through successive generations of asexual reproduction.

The grandparent cultivar Hartmann's Yellow Dignity is a light yellow with very light color on the edges of the petals, showing almost white when fully open, especially on the reverse side of the petals. The flower petals of both Hartmann's Gold Dignity and its parent Deep Yellow Hartmann's Dignity are a much richer and deeper yellow color, and the pigmentation of the flower is solid throughout, including the reverse side of the petals, as will be noted on the photographic drawing. The growing habits and response of the new cultivar are identical to Deep Yellow Hartmann's Dignity and Hartmann's Yellow Dignity.

The accompanying photographic drawings show typical inflorescence of the new cultivar, with the colors being as true as possible with color illustrations of this type. In Sheet 1, the compact flowerhead, heavy petal content, and deep and solid yellow flower color will be readily apparent.

Sheet 2 comprises a comparison photograph, with Hartmann's Gold Dignity appearing on the left, and the parent cultivar Deep Yellow Hartmann's Dignity on the right. The increased petallage and more compact flower head are clearly evident.

The following is a description of the new cultivar, with color references being made to the R.H.S. Color Chart published by the Royal Horticultural Society of London, England. The observations and color values are based on plants grown under commercial greenhouse conditions at Kirkwood, Mo.

The plant:

*Origin.*—A mutation of Deep Yellow Hartmann's Dignity.

*Classification.*—Botanical: *Chrysanthemum morifolium,* Ramat., cv. Hartmann's Gold Dignity.

*Commercial.*—Standard incurved greenhouse cut flower.

*Form.*—Perennial herbaceous upright bush.

*Height.*—40 to 48 inches when provided with 3 weeks of long-day photoperiodic treatment and optimum growing conditions.

*Growth.*—Vigorous and sturdy with very good strength and sturdy stems.

*Branching.*—Normal under natural conditions.

*Foliage.*—Abundant, 7 to 9 leaves per 10 inches of stem. Shape: Lobed lanceolate and deeply serrated. Leaf size: About $5\frac{3}{8}$ to 8 inches in length; width about $2\frac{7}{8}$ to 5 inches. Veination: Pinnate. Petioles: About $\frac{3}{4}$ to $1\frac{1}{2}$ inches long.

The bud:

*Form.*—Globular.

*Size.*—Diameter — About $\frac{3}{8}$ to $\frac{3}{4}$ inch. Depth — About $\frac{3}{8}$ to $\frac{1}{2}$ inch.

*Opening rate.*—Slow.

*Phyllaries.*—The outside of the receptacle bears many involucral bracts.

*Shape.*—Spear-shaped.

*Texture.*—Pubescent.

*Peduncle.*—Erect, about $\frac{3}{4}$ to $2\frac{1}{2}$ inches long with pubescent surface texture.

The flower:

*Blooming period.*—Year-round with photoperiod control.

*Response.*—9 week; flower maturation occurs about 59 to 63 days after initiation of short-day photoperiod treatment.

*Natural season.*—Flowering about October 27 to November 4.

*Flower type.*—Composite and incurved standard.

*Borne.*—As a head of many florets on receptacle; naturally raceme; singly when disbudded.

*Size.*—Very large when fully opened, with the diameter of the inflorescence being $5\frac{1}{2}$ to $6\frac{1}{2}$ inches.

*Shape.*—Flat when bloom first opens becoming more globular as bloom matures; very compact flowerhead.

*Petallage.*—An abundance of florets with capitulum arrangement. Form: Linear and incurved with obtuse apex. Texture: Soft. Appearance: Almost luminescent yellow. Color: The overall color of the florets at the center of the flower head at the swirl is deep yellow 12A. As the florets mature the color of the upper petals is between 9A and 9B. The internal color of the florets ranges from yellow 12A to yellow 9B. The reverse coloring of the florets is 9A, fading during maturation to 9B-9C. The petal color is a much deeper yellow than that of the grandparent cultivar Hartmann's Yellow Dignity in which the upper side of the outer florets is 4C, fading to 4D, and the upper side of the inside florets is 5B, fading to 3A.

*Discoloration after full bloom.*—Fades slightly.

*Peduncle.*—Length: About $\frac{3}{4}$ to $2\frac{1}{2}$ inches. Strength: Sturdy and upright.

*Persistence.*—Florets hang on and dry.

*Fragrance.*—Typical chrysanthemum.

*Lasting quality.*—On plant: 3 weeks. As cut flower: 10–14 days.

Reproductive organs:

*Stamens.*—Syngenesious and 5 in number. Anthers: Arrangement, connate. Filaments: About 1/16 to $\frac{1}{8}$ inch long. Color: Light yellow. Pollen: Color, yellow.

*Pistils.*—One to each ray and disc floret. Styles: About $\frac{1}{8}$ to 3/16 inch long. Stigmas: Yellow in color. Ovaries: Inferior and bicarpellate.

I claim:

1. A new and distinct cultivar of chrysanthemum plant known by the cultivar name Hartmann's Gold Dignity, as described and illustrated, and particularly characterized by its deep and solid yellow flower color, large and compact flower head, and its abundant petallage.

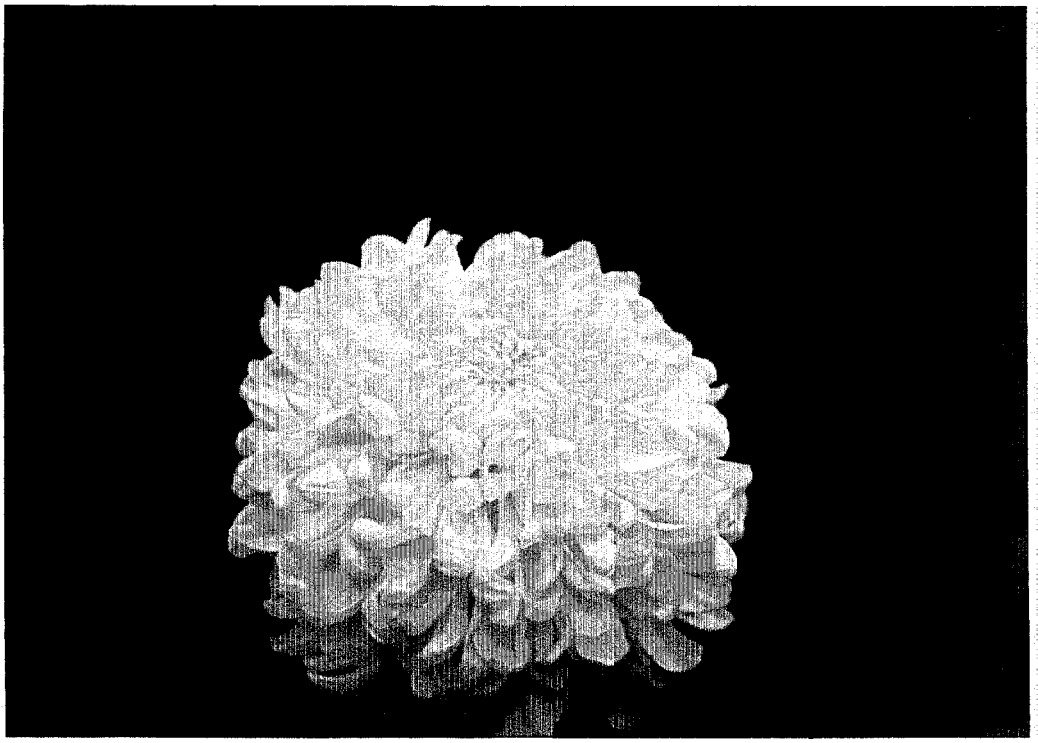

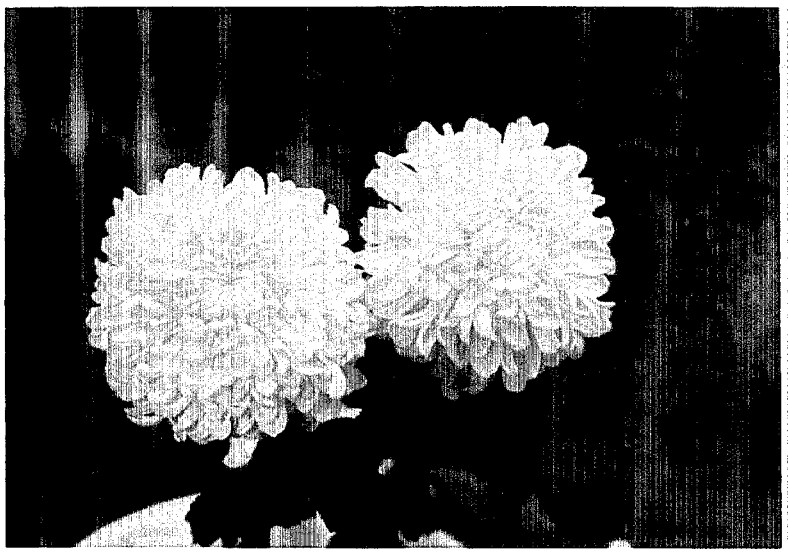

* * * * *